(12) United States Patent
Wartenfeld et al.

(10) Patent No.: US 10,789,662 B1
(45) Date of Patent: *Sep. 29, 2020

(54) FACILITATING COMPUTERIZED INTERACTIONS WITH EMRS

(71) Applicant: DBMOTION LTD., Hod Hasharon (IL)

(72) Inventors: Robert Wartenfeld, Moshav Ge'alya (IL); Ziv Ofek, Meitar (IL); Eyal Greenberg, Meitar (IL); Ziv Gome, Beit Kama (IL); Shiri Ben-Tal, Omer (IL)

(73) Assignee: ALLSCRIPTS SOFTWARE, LLC, Hod Hasharon (IL)

( * ) Notice: Subject to any disclaimer, the term of this patent is extended or adjusted under 35 U.S.C. 154(b) by 496 days.

This patent is subject to a terminal disclaimer.

(21) Appl. No.: 14/145,908

(22) Filed: Dec. 31, 2013

Related U.S. Application Data

(63) Continuation of application No. 13/208,417, filed on Aug. 12, 2011, which is a continuation-in-part of application No. 12/840,806, filed on Jul. 21, 2010.

(60) Provisional application No. 61/438,762, filed on Feb. 2, 2011.

(51) Int. Cl.
*G16H 10/60* (2018.01)
*G06Q 50/24* (2012.01)
*G06Q 10/10* (2012.01)
*G16H 10/00* (2018.01)

(52) U.S. Cl.
CPC .............. *G06Q 50/24* (2013.01); *G06Q 10/10* (2013.01); *G16H 10/00* (2018.01); *G16H 10/60* (2018.01)

(58) Field of Classification Search
CPC ................. G06Q 50/22; G06Q 50/24; G06F 19/322–327
See application file for complete search history.

(56) References Cited

U.S. PATENT DOCUMENTS

| | | |
|---|---|---|
| 7,689,916 B1 | 3/2010 | Goel et al. |
| 8,037,052 B2 | 10/2011 | Kariathungal et al. |
| 8,239,216 B2 | 8/2012 | McCallie, Jr. et al. |
| 8,949,427 B2 | 2/2015 | Dubbels et al. |
| 9,208,284 B1 | 12/2015 | Douglass |
| 9,626,262 B1 | 4/2017 | Vogel et al. |
| 9,727,348 B2 | 8/2017 | Chen et al. |
| 10,096,075 B2 | 10/2018 | Dvorak et al. |
| 10,297,343 B1 | 5/2019 | Wartenfeld et al. |
| 10,325,335 B1 | 6/2019 | Wartenfeld et al. |
| 2001/0015718 A1 | 8/2001 | Hinckley et al. |
| 2002/0032583 A1* | 3/2002 | Joao .................. 705/2 |
| 2002/0083075 A1* | 6/2002 | Brummel .............. G06Q 50/22 |
| 2003/0023717 A1 | 1/2003 | Lister |
| 2004/0122707 A1 | 6/2004 | Sabol et al. |
| 2004/0122709 A1 | 6/2004 | Avinash et al. |
| 2004/0122719 A1 | 6/2004 | Sabol et al. |
| 2004/0122787 A1 | 6/2004 | Avinash et al. |
| 2004/0141661 A1 | 7/2004 | Hanna et al. |
| 2005/0144043 A1 | 6/2005 | Holland et al. |
| 2006/0074633 A1* | 4/2006 | Mahesh ................ G06F 19/321 704/9 |
| 2006/0240771 A1 | 10/2006 | Graves et al. |
| 2006/0287890 A1 | 12/2006 | Stead et al. |
| 2007/0118540 A1 | 5/2007 | Guo |
| 2007/0174079 A1 | 7/2007 | Kraus |
| 2008/0046292 A1* | 2/2008 | Myers et al. ..................... 705/3 |
| 2008/0189496 A1 | 8/2008 | Raczynski |
| 2009/0080408 A1 | 3/2009 | Natoli et al. |
| 2009/0125555 A1 | 5/2009 | Stanis et al. |
| 2009/0177492 A1* | 7/2009 | Hasan et al. ..................... 705/3 |
| 2009/0177495 A1 | 7/2009 | Abousy et al. |
| 2009/0254572 A1 | 10/2009 | Redlich et al. |
| 2010/0161101 A1 | 6/2010 | Pouyez et al. |
| 2010/0250497 A1 | 9/2010 | Redlich et al. |
| 2011/0288877 A1 | 11/2011 | Ofek et al. |
| 2012/0215560 A1 | 8/2012 | Ofek et al. |
| 2012/0221535 A1 | 8/2012 | Dubbels et al. |

(Continued)

FOREIGN PATENT DOCUMENTS

| | | |
|---|---|---|
| DE | 10163469 A1 | 3/2003 |
| JP | 6243152 A | 9/1994 |

(Continued)

OTHER PUBLICATIONS

"Notice of Appeal for U.S. Appl. No. 14/145,905", filed Jan. 2, 2017, 2 Pages.
"Pre-Appeal Brief Conference Request for U.S. Appl. No. 14/145,905", filed Jan. 2, 2017, 5 Pages.
"Pre-Appeal Brief Conference Decision for U.S. Appl. No. 14/145,905", dated Mar. 23, 2017, 2 Pages.
"Appeal Brief for U.S. Appl. No. 14/145,905", filed May 23, 2017, 58 Pages.
"Examiner's Answer to Appeal Brief for U.S. Appl. No. 14/145,905", dated Sep. 29, 2017, 33 Pages.
"Reply Brief for U.S. Appl. No. 14/145,905", filed Nov. 29, 2017, 9 Pages.
"Appeal Decision for U.S. Appl. No. 14/145,905", dated Jun. 3, 2019, 27 Pages.

(Continued)

*Primary Examiner* — Jason S Tiedeman
(74) *Attorney, Agent, or Firm* — Medley, Behrens & Lewis, LLC

(57) ABSTRACT

A method for using a health information exchange system which stores patient record data regarding a multiplicity of patients, to serve a first plurality of EMRs each interacting with an EMR community including a set of at least one EMR, the method comprising: for each individual EMR within the first plurality of EMRs, performing a computerized context interception process using a processor to intercept context from the individual EMR and to identify there within an event whereby a health provider using the individual EMR calls up an individual patient's record from said individual EMR; and responsive to identification of the event, using a computerized output device for providing patient record data, pertaining to the individual patient, to the health provider.

19 Claims, No Drawings

(56) References Cited

U.S. PATENT DOCUMENTS

| | | |
|---|---|---|
| 2013/0218596 A1 | 8/2013 | Gome et al. |
| 2014/0088988 A1 | 3/2014 | Fairbrothers et al. |
| 2014/0188516 A1 | 7/2014 | Kamen et al. |
| 2014/0215490 A1 | 7/2014 | Mathur et al. |
| 2014/0303670 A1 | 10/2014 | Colloca |
| 2014/0350954 A1 | 11/2014 | Ellis et al. |
| 2015/0025911 A1 | 1/2015 | Altebrando et al. |
| 2015/0363554 A1 | 12/2015 | Farrell et al. |
| 2016/0054897 A1 | 2/2016 | Holmes et al. |
| 2016/0132645 A1 | 5/2016 | Charpentier et al. |
| 2017/0091388 A1 | 3/2017 | Zolla et al. |

FOREIGN PATENT DOCUMENTS

| | | |
|---|---|---|
| WO | 2007010485 A2 | 1/2007 |
| WO | 2007084502 A1 | 7/2007 |

OTHER PUBLICATIONS

"Response to the Appeal Decision for U.S. Appl. No. 14/145,905" filed Aug. 5, 2019, 8 Pages.
"Non-Final Office Action for U.S. Appl. No. 14/145,904", dated Mar. 26, 2015, 18 pages.
"Response to the Non-Final Office Action for U.S. Appl. No. 14/145,904", filed Jul. 27, 2015, 125 pages.
"Final Office Action for U.S. Appl. No. 14/145,904", dated Nov. 6, 2015, 17 pages.
"Response to the Final Office Action for U.S. Appl. No. 14/145,904", filed Feb. 8, 2016, 14 pages.
"Non-Final Office Action for U.S. Appl. No. 14/145,904", dated Jun. 16, 2016, 20 pages.
"Response to the Non-Final Office Action for U.S. Appl. No. 14/145,904", filed Sep. 16, 2016, 6 pages.
"Final Office Action for U.S. Appl. No. 14/145,904", dated Feb. 15, 2017, 25 pages.
"Notice of Appeal for U.S. Appl. No. 14/145,904", filed Jul. 17, 2017, 2 pages.
"Response to the Final Office Action for U.S. Appl. No. 14/145,904", filed Oct. 17, 2017, 17 pages.
"Non-Final Office Action for U.S. Appl. No. 14/145,904", dated Mar. 20, 2018, 9 pages.
"Response to the Non-Final Office Action for U.S. Appl. No. 14/145,904", filed Jun. 20, 2018, 26 pages.
"Final Office Action for U.S. Appl. No. 14/145,904", dated Jul. 27, 2018, 17 pages.
"Notice of Appeal for U.S. Appl. No. 14/145,904", filed Sep. 27, 2018, 2 pages.
"Pre-Appeal Brief Conference Request for U.S. Appl. No. 14/145,904", filed Sep. 27, 2018, 7 pages.
"Pre-Appeal Brief Conference Decision for U.S. Appl. No. 14/145,904", dated Nov. 21, 2018, 2 pages.
Proquest, "Search Strategy From ProQuest Dialog", Proquest Dialog, Nov. 27, 2018, 4 pages.
Hussain, et al., "Healthcare Applications Interoperability Through Implementation of HL7 Web Service Basic Profile", In 2009 Sixth International Conference on Information Technology: New Generations, IEEE Computer Society, pp. 308-313.
Lahteenmaki, et al., "Interoperability of Personal Health Records", In 31st Annual International Conference of the IEEE EMBS, Sep. 2, 2009, pp. 1726-1729.
"Notice of Allowance and Fees Due for U.S. Appl. No. 14/145,904", dated Jan. 4, 2019, 10 pages.
"Preliminary Amendment for U.S. Appl. No. 14/145,906", filed Mar. 17, 2014, 7 Pages.
"Non-Final Office Action for U.S. Appl. No. 14/145,906", dated Mar. 27, 2015, 18 Pages.
"Response to the Non-Final Office Action for U.S. Appl. No. 14/145,906", filed Jul. 27, 2015, 126 Pages.
"Final Office Action for U.S. Appl. No. 14/145,906", dated Nov. 5, 2015, 17 Pages.
"Response to the Final Office Action for U.S. Appl. No. 14/145,906", filed Feb. 5, 2016, 17 Pages.
"Non-Final Office Action for U.S. Appl. No. 14/145,906", dated Jun. 15, 2016, 19 Pages.
"Response to the Non-Final Office Action for U.S. Appl. No. 14/145,906", filed Sep. 15, 2016, 10 Pages.
"Final Office Action for U.S. Appl. No. 14/145,906", dated Oct. 3, 2016, 26 Pages.
"Notice of Appeal for U.S. Appl. No. 14/145,906", filed Jan. 2, 2017, 2 Pages.
"Pre-Appeal Brief Conference Request for U.S. Appl. No. 14/145,906", filed Jan. 2, 2017, 3 Pages.
"Pre-Appeal Brief Conference Decision for U.S. Appl. No. 14/145,906", dated Mar. 23, 2017, 2 Pages.
"Appeal Brief for U.S. Appl. No. 14/145,906", filed Jun. 23, 2017, 61 Pages.
"Examiner's Answer to Appeal Brief for U.S. Appl. No. 14/145,906", dated Nov. 14, 2017, 28 Pages.
"Reply Brief for U.S. Appl. No. 14/145,906", filed Jan. 16, 2018, 15 Pages.
"Preliminary Amendment for U.S. Appl. No. 14/145,907", filed Mar. 17, 2014, 7 Pages.
"Non-Final Office Action for U.S. Appl. No. 14/145,907", dated Mar. 25, 2015, 18 Pages.
"Response to the Non-Final Office Action for U.S. Appl. No. 14/145,907", filed Jul. 27, 2015, 125 Pages.
"Final Office Action for U.S. Appl. No. 14/145,907", dated Nov. 5, 2015, 17 Pages.
"Response to the Final Office Action for U.S. Appl. No. 14/145,907", filed Feb. 5, 2016, 19 Pages.
"Non-Final Office Action for U.S. Appl. No. 14/145,907", dated Jul. 21, 2016, 20 Pages.
"Response to the Non-Final Office Action for U.S. Appl. No. 14/145,907", filed Oct. 21, 2016, 11 Pages.
"Final Office Action for U.S. Appl. No. 14/145,907", dated Feb. 7, 2017, 28 Pages.
"Response to the Final Office Action for U.S. Appl. No. 14/145,907", filed May 8, 2017, 36 Pages.
"Non-Final Office Action for U.S. Appl. No. 12/840,806", dated Mar. 20, 2012, 14 Pages.
"Response to the Non-Final Office Action for U.S. Appl. No. 12/840,806", filed Jun. 12, 2012, 17 Pages.
Computer Methods and Programs in Biomedicine, 2009, 93 (3), 297-312 "XML technologies for the Omaha System: a data model, a Java tool and several case studies supporting home healthcare". Vittorini Pierpaolo; Tarquinio Antonietta; di Orio Ferdinando.
Digital Society, 2009. ICDS '09. Third International Conference, 168-173 "Semantic Exchange of Medicinal Data: A Way Towards Open Healthcare Systems". Puustjarvi, J and Puustjarvi.
Engineering in Medicine and Biology Society, 2009. EMBC 2009. Annual International Conference of the IEEE, 1726-1729 "Interoperability of personal health records". Lahteenmaki, Jaakko; Leppanen, Juha and Kaijanranta, Hannu.
Information Technology: New Generations, 2009. ITNG '09. Sixth International Conference; 308-313 "Healthcare Applications Interoperability through Implementation of HL7 Web Service Basic profile" Hussain, M; Afzal, M; Ahmad, H.F; Khalid, N and Ali A.
Computer-Based Medical Systems, 2009. CBMS 2009. 22nd IEEE International Symposium; 1-6 "Ontology-based approach to achieve semantic interoperability on exchanging and integrating information about the patient clinical evolution" Miyoshi, N, Ferreira, A and Felipe, J.C.
Computer-Based Medical Systems, 2009. CBMS 2009. 22nd IEEE International Symposium; 1-6 "Semantic biological image management and analysis" Chubb, C, Inagaki, Y, Cotman, C, Cummings, B and Sheu, P.C.
Healthcare Services Specification Project (HSSP) Service Functional Model (SFM) Specification—Decision Support Service (DSS), Version 1.0, Sep. 24, 2006, available on the World Wide Web. http://www.nlm.nih.gov/research/umls/.

(56) References Cited

OTHER PUBLICATIONS

"Final Office Action for U.S. Appl. No. 12/840,806", dated Dec. 7, 2012, 20 Pages.
"Non-Final Office Action for U.S. Appl. No. 13/208,417", dated Feb. 4, 2013, 28 Pages.
"Response to the Final Office Action for U.S. Appl. No. 12/840,806", filed May 3, 2013, 18 Pages.
"Non-Final Office Action for U.S. Appl. No. 12/840,806", dated Jun. 17, 2014, 20 Pages.
"Response to the Non-Final Office Action for U.S. Appl. No. 12/840,806", filed Oct. 17, 2014, 3 Pages.
"Non-Final Office Action for U.S. Appl. No. 12/840,806", dated Feb. 11, 2015, 17 Pages.
"Response to the Non-Final Office Action for U.S. Appl. No. 12/840,806", filed Jul. 13, 2015, 5 Pages.
"Final Office Action for U.S. Appl. No. 12/840,806", dated Oct. 20, 2015, 20 Pages.
"Notice of Appeal for U.S. Appl. No. 12/840,806", filed Jan. 20, 2016, 2 Pages.
"Appeal Brief for U.S. Appl. No. 12/840,806", filed May 20, 2016, 30 Pages.
"Non-Final Office Action for U.S. Appl. No. 12/840,806", dated Nov. 4, 2016, 17 Pages.
"Response to the Non-Final Office Action for U.S. Appl. No. 12/840,806", filed Mar. 6, 2017, 7 Pages.
"Final Office Action for U.S. Appl. No. 12/840,806", dated Jun. 15, 2017, 24 Pages.
"Notice of Appeal for U.S. Appl. No. 12/840,806", filed Oct. 16, 2017, 2 Pages.
"Appeal Brief for U.S. Appl. No. 12/840,806", filed Jan. 16, 2018, 29 Pages.
"Examiner's Answer to Appeal Brief for U.S. Appl. No. 12/840,806", dated May 25, 2018, 22 Pages.
"Reply Brief for U.S. Appl. No. 12/840,806", filed Jul. 25, 2018, 6 Pages.
"Appeal Decision for U.S. Appl. No. 12/840,806", dated Nov. 30, 2018, 12 Pages.
"Response to the Non-Final Office Action for U.S. Appl. No. 13/208,417", filed Jul. 5, 2013, 19 Pages.
"Final Office Action for U.S. Appl. No. 13/208,417", dated Nov. 8, 2013, 16 Pages.
"Response to the Final Office Action for U.S. Appl. No. 13/208,417", filed Mar. 10, 2014, 7 Pages.
"Advisory Action for U.S. Appl. No. 13/208,417", dated Mar. 19, 2014, 2 Pages.
"Non-Final Office Action for U.S. Appl. No. 13/208,417", dated Oct. 7, 2014, 13 Pages.
"Response to the Non-Final Office Action for U.S. Appl. No. 13/208,417", filed Feb. 9, 2015, 7 Pages.
"Final Office Action for U.S. Appl. No. 13/208,417", dated Jun. 3, 2015, 17 Pages.
"Notice of Appeal for U.S. Appl. No. 13/208,417", filed Sep. 3, 2015, 2 Pages.
"Appeal Brief for U.S. Appl. No. 13/208,417", filed Feb. 3, 2016, 26 Pages.
"Examiner's Answer to Appeal Brief for U.S. Appl. No. 13/208,417", dated Aug. 25, 2016, 18 Pages.
"Reply Brief for U.S. Appl. No. 13/208,417", filed Oct. 25, 2016, 11 Pages.
"Request for Oral Hearing for U.S. Appl. No. 13/208,417", filed Oct. 25, 2016, 2 Pages.
"Record of Oral Hearing for U.S. Appl. No. 13/208,417", dated Dec. 25, 2018, 12 Pages.
"Appeal Decision for U.S. Appl. No. 13/208,417", dated Dec. 20, 2018, 11 Pages.
"Preliminary Amendment for U.S. Appl. No. 14/145,905", filed Mar. 17, 2014, 7 Pages.
"Non-Final Office Action for U.S. Appl. No. 14/145,905", dated Mar. 12, 2015, 17 Pages.
"Response to the Non-Final Office Action for U.S. Appl. No. 14/145,905", filed Jul. 11, 2015, 8 Pages.
"Final Office Action for U.S. Appl. No. 14/145,905", dated Oct. 21, 2015, 17 Pages.
"Response to the Final Office Action for U.S. Appl. No. 14/145,905", filed Feb. 22, 2016, 16 Pages.
"Non-Final Office Action for U.S. Appl. No. 14/145,905", dated Jun. 16, 2016, 26 Pages.
"Response to the Non-Final Office Action for U.S. Appl. No. 14/145,905", filed Sep. 16, 2016, 6 Pages.
"Final Office Action for U.S. Appl. No. 14/145,905", dated Oct. 3, 2016, 32 Pages.
"Non-Final Office Action for U.S. Appl. No. 14/145,907", dated Sep. 7, 2017, 7 Pages.
"Response to the Non-Final Office Action for U.S. Appl. No. 14/145,907", filed Jan. 8, 2018, 32 Pages.
"Final Office Action for U.S. Appl. No. 14/145,907", dated May 1, 2018, 11 Pages.
"Preliminary Amendment for U.S. Appl. No. 14/145,903", filed Mar. 17, 2014, 7 Pages.
"Non-Final Office Action for U.S. Appl. No. 14/145,903", dated Mar. 18, 2015, 17 Pages.
"Response to the Non-Final Office Action for U.S. Appl. No. 14/145,903", filed Jul. 20, 2015, 10 Pages.
"Final Office Action for U.S. Appl. No. 14/145,903", dated Nov. 5, 2015, 17 Pages.
"Response to the Final Office Action for U.S. Appl. No. 14/145,903", filed Feb. 5, 2016, 17 Pages.
"Non-Final Office Action for U.S. Appl. No. 14/145,903", dated Apr. 6, 2016, 18 Pages.
"Notice of Appeal for U.S. Appl. No. 14/145,903", filed Aug. 8, 2016, 2 Pages.
"Pre-Appeal Brief Conference Request for U.S. Appl. No. 14/145,903", filed Aug. 8, 2016, 3 Pages.
"Pre-Appeal Brief Conference Decision for U.S. Appl. No. 14/145,903", dated Sep. 26, 2016, 2 Pages.
"Appeal Brief for U.S. Appl. No. 14/145,903", filed Oct. 26, 2016, 44 Pages.
"Examiner's Answer to Appeal Brief for U.S. Appl. No. 14/145,903", dated Feb. 8, 2017, 27 Pages.
"Reply Brief for U.S. Appl. No. 14/145,903", filed Apr. 10, 2017, 7 Pages.
"Appeal Decision for U.S. Appl. No. 14/145,903", dated Nov. 30, 2018, 12 Pages.
"Notice of Allowance and Fees Due for U.S. Appl. No. 14/145,903", dated Feb. 15, 2019, 8 Pages.
"Preliminary Amendment for U.S. Appl. No. 14/145,904", filed Mar. 17, 2014, 7 pages.
"Preliminary Amendment for U.S. Appl. No. 16/391,371", filed Apr. 23, 2019, 8 pages.
"Preliminary Amendment for U.S. Appl. No. 15/648,096", filed Oct. 17, 2017, 7 Pages.
"Restriction Requirement for U.S. Appl. No. 15/648,096", dated Nov. 17, 2017, 9 Pages.
"Response to the Restriction Requirement for U.S. Appl. No. 15/648,096", filed Dec. 31, 2017, 9 Pages.
"Final Office Action for U.S. Appl. No. 15/648,096", dated Mar. 21, 2018, 14 Pages.
"Non-Final Office Action for U.S. Appl. No. 15/648,096", dated Apr. 6, 2018, 14 Pages.
"Response to the Non-Final Office Action for U.S. Appl. No. 15/648,096", filed Jul. 5, 2018, 4 Pages.
"Final Office Action for U.S. Appl. No. 15/648,096", dated Sep. 11, 2018, 17 Pages.
"Response to the Final Office Action for U.S. Appl. No. 15/648,096", filed Nov. 8, 2018, 21 Pages.
"Advisory Action for U.S. Appl. No. 15/648,096", dated Nov. 27, 2018, 3 Pages.
"Notice of Appeal for U.S. Appl. No. 15/648,096", filed Dec. 11, 2018, 2 Pages.
"Pre-Appeal Brief Conference Request for U.S. Appl. No. 15/648,096", filed Dec. 11, 2018, 7 Pages.

(56) References Cited

OTHER PUBLICATIONS

"Pre-Appeal Brief Conference Decision for U.S. Appl. No. 15/648,096", dated Feb. 7, 2019, 2 Pages.
"Appeal Brief for U.S. Appl. No. 15/648,096", filed Mar. 7, 2019, 21 Pages.
"Non-Final Office Action for U.S. Appl. No. 15/648,096", dated May 30, 2019, 10 Pages.
"Response to the Non-Final Office Action for U.S. Appl. No. 15/648,096", filed Aug. 30, 2019, 12 Pages.
"Notice of Allowance and Fees Due for U.S. Appl. No. 15/648,096", dated Nov. 14, 2019, 15 Pages.
"Non-Final Office Action for U.S. Appl. No. 15/361,823", dated Mar. 21, 2019, 20 Pages.
"Response to the Non-Final Office Action for U.S. Appl. No. 15/361,823", filed Aug. 21, 2019, 13 Pages.
"Non-Final Office Action for U.S. Appl. No. 15/361,803", dated Apr. 9, 2019, 12 Pages.
"Response to the Non-Final Office Action for U.S. Appl. No. 15/361,803", filed Aug. 9, 2019, 9 Pages.
"Final Office Action for U.S. Appl. No. 15/361,803", dated Oct. 3, 2019, 13 Pages.
"Non-Final Office Action for U.S. Appl. No. 15/361,788", dated Sep. 28, 2018, 31 Pages.
"Response to the Non-Final Office Action for U.S. Appl. No. 15/361,788", filed Dec. 28, 2018, 10 Pages.
"Final Office Action for U.S. Appl. No. 15/361,788", dated Apr. 3, 2019, 36 Pages.
"Response to the Final Office Action for U.S. Appl. No. 15/361,788", filed Aug. 5, 2019, 15 Pages.
"Non-Final Office Action for U.S. Appl. No. 15/361,788", dated Aug. 15, 2019, 36 Pages.
"Response to the Non-Final Office Action for U.S. Appl. No. 15/361,788", filed Nov. 15, 2019, 15 Pages.
"Final Office Action for U.S. Appl. No. 15/361,823", dated Nov. 26, 2019, 21 Pages.
"Response to the Final Office Action for U.S. Appl. No. 15/361,803", filed Jan. 3, 2020, 16 Pages.

\* cited by examiner

FACILITATING COMPUTERIZED INTERACTIONS WITH EMRS

REFERENCE TO CO-PENDING APPLICATIONS

The present application is a U.S. continuation patent application of, and claims priority under 35 U.S.C. § 120 to, U.S. nonprovisional patent application Ser. No. 13/208,417, filed Aug. 12, 2011, which '417 application published as U.S. patent application publication no. 2012/0215560, which '560 publication is incorporated herein by reference, and which '417 application is a U.S. continuation-in-part patent application of, and claims priority under 35 U.S.C. § 120 to, U.S. nonprovisional patent application Ser. No. 12/840,806, filed Jul. 21, 2010, which '806 application published as U.S. patent application publication no. 2011/0288877, which '877 publication is incorporated by reference herein. The '417 application further is a U.S. nonprovisional patent application of, and claims priority under 35 U.S.C. § 119 (e) to, U.S. provisional patent application Ser. No. 61/438,762, filed Feb. 2, 2011, which provisional patent application is incorporated by reference herein. Moreover, the disclosure of the priority provisional patent document, namely, the '762 application, is set forth in the Appendix hereto, which is incorporated by reference herein.

FIELD OF THE INVENTION

The present invention relates generally to systems for processing medical information and more particularly to computerized interactions with EMRs.

BACKGROUND OF THE INVENTION

Conventionally, information is transferred between an HIE and EMR via messages exchanged between the two systems. For example, an EMR may know how to import lab results from an HIES. An EMR may provide a tab in its main application, sometimes known as the "community tab" which enables a user to view, but not manipulate or import, HIE-provided information about a patient. Varying medical technology between the HIE and EMR, combined with a lack of ability to semantically resolve the variation, may impose limitations to these modes of information transfer.

According to Wikipedia, an Enterprise Master Patient Index (EMPI) is "a form of customer data integration (CDI) specific to the healthcare industry. Healthcare organizations or groups of them will implement EMPI to identify, match, merge, de-duplicate, and cleanse patient records to create a master index that may be used to obtain a complete and single view of a patient. The EMPI will create a unique identifier for each patient and maintain a mapping to the identifiers used in each record's respective system." It has been claimed that by using an EMPI for "correctly matching patient records from disparate systems and different organizations", it is possible to obtain "a complete view of a patient".

Known technologies relevant to the field of the invention include context management, single sign-on, CCOW or Screen capturing method for context interception.

Other state of the art health information exchange and integration systems, and conventional technology pertaining to certain embodiments of the present invention, are described in the following publications inter alia:
1. US20070118540
2. US20090125555
3. US20080189496
4. WO 2007010485
5. JP6243152
6. DE10163469
7. US20040141661
8. US20090080408
9. US20040122709
10. US20040122719
11. US20040122787
12. US20040122707
13. Published US Application US20080046292;
14. Published US Application US20050144043; and
15. Published PCT Application WO/2007/084502.

Non-Patent Literature describing health information exchange through the use of semantic technology includes:
Comput Methods Programs Biomed., 2009, 93 (3), 297-312 XML technologies for the Omaha System: a data model, a Java tool and several case studies supporting home healthcare Vittorini Pierpaolo; Tarquinio Antonietta; di Orio Ferdinando
Digital Society, 2009. ICDS '09. Third International Conference, 168-173 Semantic Exchange of Medicinal Data: A Way Towards Open Healthcare Systems Puustjarvi, J and Puustjarvi, L
Engineering in Medicine and Biology Society, 2009. EMBC 2009. Annual International Conference of the IEEE, 1726-1729 Interoperability of personal health records Lahteenmaki, Jaakko; Leppanen, Juha and Kaijanranta, Hannu
Information Technology: New Generations, 2009. ITNG '09. Sixth International Conference; 308-313 Healthcare Applications Interoperability through Implementation of HL7 Web Service Basic Profile Hussain, M; Afzal, M; Ahmad, H. F; Khalid, N and Ali, A
Computer-Based Medical Systems, 2009. CBMS 2009. 22nd IEEE International Symposium; 1-6 Ontology-based approach to achieve semantic interoperability on exchanging and integrating information about the patient clinical evolution Miyoshi, N, Ferreira, A and Felipe, J. C
Computer-Based Medical Systems, 2009. CBMS 2009. 22nd IEEE International Symposium; 1-6 Semantic biological image management and analysis Chubb, C, Inagaki, Y, Cotman, C, Cummings, B and Sheu, P. C
Lähteenmäki, Jaakko, Leppänen, Juha, Kaijanranta, Hannu, "Interoperability of Personal Health Records" (2009) 31st Annual Int. Conference of the IEEE Engineering in Medicine and Biology Society, EMBC'09, Minneapolis, Minn., USA, 2-6 September, 2009, EMBC'09 DVD, 1726-1729.
Miyoshi, N. Ferreira, A. Felipe, J. C. , "Ontology-based approach to achieve semantic interoperability on exchanging and integrating information about the patient clinical evolution", Computer-Based Medical Systems, 2009. CBMS 2009. 22nd IEEE International Symposium on Issue Date: 2-5 Aug. 2009
Healthcare Services Specification Project (HSSP) Service Functional Model (SFM) Specification-Decision Support Service (DSS), Version 1.0, Sep. 27, 2006, available on the World Wide Web.

The disclosures of all publications and patent documents mentioned in the specification, and of the publications and patent documents cited therein directly or indirectly, are hereby incorporated by reference.

SUMMARY OF THE INVENTION

Certain embodiments of the present invention seek to provide a technical solution for the problem of allowing medical data to be effectively retrieved, stored, and presented to medical service providing users where the medical data exists in digital form within a plethora of non-compatible, partially overlapping software systems which are constantly being updated.

Certain embodiments of the present invention seek to provide an interoperability solution for medical databases, providing a health information exchange system typically storing complete, single and harmonized patient records, and easing access thereto by bringing relevant information to a user at points in time in which that information is useful and as part of her or his workflows.

Certain embodiments of the present invention seek to bring relevant context-based information from inside the health information exchange system to a user e.g. physician's working environment and workflows (typically EMR), rather having the physician leave his working environment and search for the information he needs in a Clinical Viewer as an external application.

Certain embodiments of the present invention seek to enhance effective software compatibility including reducing dependency on EMR vendors to customize their software products in order to integrate with the health information exchange system platform (Button, Smart Access, and other services).

Certain embodiments of the present invention seek to provide easy and efficient access to specific context-based patient information eliminating the need to navigate through many patient's views in an external application.

Generally, Health Information Exchange (HIE) is defined as the mobilization of healthcare information electronically across organizations within a region, community or hospital system. HIE provides the capability to electronically move clinical information among disparate health care information systems while maintaining the meaning of the information being exchanged. The goal of HIE is to facilitate access to and retrieval of clinical data to provide safer, more timely, efficient, effective, equitable, patient-centered care. To meet this goal, HIE providers develop computerized infrastructures and applications that enable the information exchange and viewing of exchanged information. As HIE solutions complement the EMR applications, the EMR and HIE vendors are looking for ways to integrate with each other in order to enable:

1. Data exchange from the EMR the HIE and vice versa
2. Integrate the information hold in hold in the IHE within the EMR application and user workflow
3. Enrich EMR capabilities with the HIE solutions and services.

When an HIE solution is integrated with the EMR, both accessibility and User Context may be taken into account.

Certain embodiments of the present invention seek to provide an SOA-based platform that enables healthcare organizations and health information exchanges (HIEs) to integrate their information assets, through the creation of a virtual patient record by logically connecting a group of care providers and organizations without requiring the replacement of existing information systems. By providing ubiquitous access to integrated patient information, the solution virtually bridges gaps that often exist between inpatient/acute care and community care.

Typically, a single, virtual patient record contains complete and harmonized patient data by logically connecting a group of care providers and organizations without requiring the replacement of existing information systems. Smooth and easy access to the care-critical information stored in the HIE should be facilitated, by providing a user with relevant patient information at the point in time it is needed, as part of the clinical workflow.

The system shown and described herein may perform any or all of the above functionalities:

Provide important, relevant, context-based information from the HIE within a physicians' work environment and workflows (typically their EMRs)—as opposed to having the physicians leave their work environments and enter the HIE's Clinical Viewer functionality as an external application to search for the information needed.

Reduce the HIE's dependency on EMR vendors to customize their products in order to integrate with the HIE's platform (e.g. launch button, SSO, services).

Provide efficient access to specific context-based patient information, thereby eliminating the need to navigate through multiple clinical views in an external application such as a dbMotion Viewer.

The SmartAgent is a client application that is designed to meet the EMR users' need to get comprehensive and relevant clinical information on patients from sources of information which are not in their EMR, and in addition to serve as a gateway to HIE applications and solutions.

The client application, typically installed on the user's machine, is termed herein a SmartAgent client.

Examples of use scenarios include but are not limited to the following:

1. Smart Button within User , Patient and System Context: User opens a patient record in his EMR. SmartAgent, which is installed in his client machine, "captures" the patient identifier (MRN) , the User Context (Username/Role) and the System context (SystemID) and calls a VPO Analyzer web service or Virtual Patient Object Clinical Data Web Service) that identifies the System, user and the patient. The user is authorized and the patient is found in the health information exchange system. The Client SmartAgent gets the response and presents a Floating Button. The Floating button includes Link to Launch Viewer with user and patient context. The User presses the button and seamlessly accesses the health information exchange system's Clinical Viewer.

2. VPO Analyzer attention rules : In order to bring more relevant information to the user, smart evaluations are typically provided on the VPO in the context of the user, patient and system. One of the Analyzer's attention rules may be "Exclude System Data" which excludes from the VPO Data that exists in the physician's own system. The response is "Clean" data excluding what a user can see in his EMR, which may be presented within the Results or Viewer Panes. The rule is typically constructed and operative to analyze the patient's clinical data and to alert the user in the SmartAgent client application that information that meets the rule exists and is available for viewing.

3. Semantic Search: A user may for example be looking for data on Diabetes in the health information exchange system. To do that he enables a search option in the floating toolbar and type the phrase "Dia". Search suggestions are presented and user selects the "Diabetes" Suggestion. As a result a "Results and Navigation" pane opens and presents the results for Diabetes from the Patient's VPO organized by Clinical Aspects (Medications, Problems, Population Membership, etc.). User presses "Diabetes" population and the Diabetes View is opened in the View panel.

4. Data Presentation and Launch Viewer: Any information found may be presented in a Data and Navigation Panel.

The information is organized according to the different clinical aspects (Laboratory, Medications, etc.) and evaluation aspects (Population membership, Metrics, Notifications, Alerts etc.). The clinical aspects and actual presented data may constitute a link to a relevant page in the health information exchange system's Clinical Viewer. The user can see under a Laboratory Results menu, a result for hbA1c from, say, a previous week. Aside from the result, 2 buttons may be provided, one to open the Laboratory Clinical View and another to open the Lab Result Page with the hbA1c history.

The present invention also typically includes at least the following embodiments:

a. A computerized system for supplying a human user with relevant, context-based patient information within the user's work environment and workflows.

b. A system according to embodiment a wherein the user's work environment includes at least one EMR.

c. A system according to embodiment b which does not require customization of the EMR.

d. A system according to embodiment 'a' which supplies information without requiring the user to navigate through multiple clinical views in an external application.

e. A system according to embodiment 'a' wherein the system includes a proactive apparatus which operates proactively, responsive to user context operations, to present relevant clinical information.

f. A system according to embodiment 'a' wherein the system includes a processor operative to select relevant information including performing a computerized analysis of a computerized patient record and deriving, from the analysis, relevant clinical information which is presented to the user, whereas other clinical information is not presented to the user.

g. A system according to embodiment 'f' wherein differentiation of relevant clinical information from other clinical information is based on at least one of the following: user context, profile, patient illness, ward context, EMR Workflow Context.

h. A system according to embodiment 'a' and wherein the system is operative to provide information, within the workflow, on overall patient events and evaluations for each individual physician or user.

i A system according to embodiment 'a' and also comprising at least some aspects of a skin application shown and described herein.

j. A computerized method for supplying a human user with relevant, context-based patient information within the user's work environment and workflows.

k. A method according to embodiment 'j' wherein the user's work environment includes at least one EMR.

l. A method according to embodiment 'k' which does not require customization of the EMR.

m. A method according to embodiment 'j' which supplies information without requiring the user to navigate through multiple clinical views in an external application.

n. A method according to embodiment 'j' wherein the method includes a proactive apparatus which operates proactively, responsive to user context operations, to present relevant clinical information.

o. A method according to embodiment 'j' wherein the method includes a processor operative to select relevant information including performing a computerized analysis of a computerized patient record and deriving, from the analysis, relevant clinical information which is presented to the user, whereas other clinical information is not presented to the user.

p. A method according to embodiment 'o' wherein differentiation of relevant clinical information from other clinical information is based on at least one of the following: user context, profile, patient illness, ward context, EMR Workflow Context.

q. A method according to embodiment 'a' and wherein the system is operative to provide information, within the workflow, on overall patient events and evaluations for each individual physician or user.

r. A method according to embodiment 'j' and also comprising at least some aspects of a skin application shown and described herein.

s. A computer program product, comprising a computer usable medium having a computer readable program code embodied therein, the computer readable program code adapted to be executed to implement any of the methods shown and described herein.

Certain embodiments of the present invention seek to provide a decision making system including a system of logic including hierarchical semantic relationships, a plurality of systems of medical information which are provided in a plurality of local terminologies respectively, and a decision making apparatus for transforming the medical information in the local terminologies to transformed information usable by the system of logic and for using the system of logic to make at least one decision based on the transformed information, without translating the system of logic into the plurality of local terminologies. The term "terminology" is intended to include any scheme for representing medical information. The following terms and other terms defined herein may be construed either in accordance with any definition thereof appearing in the prior art literature or in accordance with the specification, or as follows:

Classification Type—A base set of classifications which all others derive from. The existing classifications are:
Candidate—represents a new population element entering the system.
ActiveMember—represents a member of the population currently being monitored
DormantMember—represents a member who is "sleeping" or currently active but not being monitored (in a dormant state)

Evaluation Task—an evaluation task combines a set of executable rules, an evaluation goal, activation, and a set of triggering rule subscriptions. When a member is associated with a task (by having a specific classification) the triggering rule subscriptions are sent to the Data Event Monitor for that member. When task processing is activated, if that member has had any matching triggering rules fire, the task is sent to be processed (along with the member details).

Member—The population element of a specific Guard, each member is tagged with its population source and contains a list of classifications.

Member Classification—Guard evaluation tasks are grouped by classifications. If a member belongs to a specific classification, that member has certain tasks associated with him or her.

Population Source—the source of members for the Guard, could be an external list, an enrollment service, or a data event monitor.

Triggering Rule Subscription—subscription for the Abstract Rule Monitor, contains a Pattern Rule Identifier and a set of subscription arguments.

Schedule—an alarm (scheduled or event based) used to activate processing for a particular evaluation task (or set of evaluation tasks).

DEM—data event monitor e.g. as described herein
EMPI—Conventional Enterprise Master Patient Index service
Principal Index—aka (also termed herein) Leading Index
VIA—a commercial Virtual Identity Aggregation service provided by DBMotion Inc., Israel
ACEI—angiotensin-converting enzyme inhibitors
LVS—Left Ventricular Systolic
LVSD—Left Ventricular Systolic Dysfunction
DBMotion—refers to a functionality which is either commercially available from DBMotion Inc., Israel and/ or is shown and described herein. Other definitions, acronyms, and abbreviations useful in understanding certain embodiments of the present invention, are provided in the table of FIG. 2 of incorporated U.S. patent application publication no. 2012/0215560.

In accordance with an aspect of the invention, there is provided a health information exchange system comprising an apparatus for archiving health information using a health information encoding procedure only if the health information fulfills a criterion of frequent use; and an apparatus for using a first procedure to respond to queries pertaining to the health information which fulfills the criterion of frequent use and using a second procedure to respond to queries not pertaining to the health information which fulfills the criterion of frequent use.

In accordance with an aspect of the invention, there is further provided a health information exchange system comprising an ontological apparatus for defining and storing ontological link elements ontologically linking between individual health care information items within a first population of health care information items; an apparatus for receiving a second population of health care information items and for associating at least some individual items in the second population, with corresponding individual items within the first population of health care information items; and an apparatus for responding to queries regarding particular information items in the second population including translating the particular information items into items in the first population corresponding to the particular information items and using link elements linking the items in the first population corresponding to the particular information items to generate data pertaining to the particular information items in the second population.

In accordance with an embodiment of the invention, there is provided a system comprising an apparatus for making at least one health decision based on the queries.

In accordance with an embodiment of the invention, there is further provided a system also comprising apparatus for implementing the at least one health decision.

In accordance with an embodiment of the invention, there is further provided a system also comprising apparatus for making at least one health decision based on the queries.

In accordance with an embodiment of the invention, there is further provided a system also comprising apparatus for implementing the at least one health decision.

In accordance with an aspect of the invention, there is provided a health information exchange method comprising archiving health information using a health information encoding procedure only if the health information fulfills a criterion of frequent use; and using a first procedure to respond to queries pertaining to the health information which fulfills the criterion of frequent use and using a second procedure to respond to queries not pertaining to the health information which fulfills the criterion of frequent use. In accordance with an aspect of the invention, there is provided a health information exchange method comprising defining and storing link elements linking between individual health care information items within a first population of health care information items; receiving a second population of health care information items and associating at least some individual items in the second population, with corresponding individual items within the first population of health care information items; and responding to queries regarding particular information items in the second population including translating the particular information items into items in the first population corresponding to the particular information items and using link elements linking the items in the first population corresponding to the particular information items to generate data pertaining to the particular information items in the second population.

In accordance with an embodiment of the invention, there is further provided a method also comprising making at least one health decision based on the queries.

In accordance with an embodiment of the invention, there is still further provided a method also comprising implementing the at least one health decision.

In accordance with an embodiment of the invention, there is yet further provided a method also comprising making at least one health decision based on the queries.

In accordance with an embodiment of the invention, there is yet further provided a method also comprising implementing the at least one health decision.

In accordance with an aspect of the invention, there is provided a computer program product, comprising a computer usable medium having a computer readable program code embodied therein, the computer readable program code adapted to be executed to implement a health information exchange method comprising archiving health information using a health information encoding procedure only if the health information fulfills a criterion of frequent use; and using a first procedure to respond to queries pertaining to the health information which fulfills the criterion of frequent use and using a second procedure to respond to queries not pertaining to the health information which fulfills the criterion of frequent use.

In accordance with an aspect of the invention, there is yet further provided a computer program product, comprising a computer usable medium having a computer readable program code embodied therein, the computer readable program code adapted to be executed to implement a health information exchange method comprising defining and storing link elements linking between individual health care information items within a first population of health care information items; receiving a second population of health care information items and for associating at least some individual items in the second population, with corresponding individual items within the first population of health care information items; and responding to queries regarding particular information items in the second population including translating the particular information items into items in the first population corresponding to the particular information items and using link elements linking the items in the first population corresponding to the particular information items to generate data pertaining to the particular information items in the second population.

In accordance with an embodiment of the invention, there is yet further provided a computer program product wherein the method also comprises making at least one health decision based on the queries.

In accordance with an embodiment of the invention, there is yet further provided a computer program product wherein the method also comprises implementing the at least one health decision.

In accordance with an embodiment of the invention, there is yet further provided a computer program product wherein the method also comprises making at least one health decision based on the queries.

In accordance with an embodiment of the invention, there is yet further provided a computer program product wherein the method also comprises implementing the at least one health decision.

In accordance with an embodiment of the invention, there is yet further provided a method wherein the second population of health care information items are expressed in a local terminology and are mapped to a baseline terminology in which the first population of health care information items are expressed, to enable terminology interoperability at least when responding to queries.

In accordance with an embodiment of the invention, there is yet further provided a method wherein the baseline terminology is semantically enriched by associating semantic information therewith, the method also comprising generating conclusions about health information expressed in at least one local terminology by using the semantic information rather than by defining semantic relations for the local terminology.

In accordance with an embodiment of the invention, there is yet further provided a system in which only a subset of a universe of health information is archived.

In accordance with an embodiment of the invention, there is yet further provided a system wherein the apparatus for responding to queries uses a first procedure to respond to queries pertaining to the subset and uses a second procedure to respond to queries not pertaining to the universe of health information but not pertaining to the subset.

In accordance with an embodiment of the invention, there is yet further provided a system also including an end user interface allowing end users to define rules; and a decision support subsystem (DSS) interacting with the end user interface and using semantic capabilities of a baseline terminology in which the first population of health information items is encoded, to simplify definition of rules by the end users.

In accordance with an embodiment of the invention, there is yet further provided a system wherein the decision support subsystem comprises an Enterprise DSS which has a process cycle and which uses DSS rules to define all phases in the process cycle.

In accordance with an embodiment of the invention, there is yet further provided a method wherein the translating and the using is applied to a use case involving processing of Smart Guard Adapters, the processing including at least one of developing, defining and configuring.

In accordance with an embodiment of the invention, there is yet further provided a method wherein the translating and the using is applied to a use case involving a SmartWatch System, the use case including at least one of processing and monitoring health of the system.

In accordance with an embodiment of the invention, there is yet further provided a method wherein the translating and the using are applied to a use case involving Managing Guard runtime.

In accordance with an embodiment of the invention, there is yet further provided a method wherein the translating and the using are applied to a use case involving applying Guard changes.

In accordance with an embodiment of the invention, there is yet further provided a method wherein the translating and the using are applied to a use case involving task activation based upon a schedule.

In accordance with an embodiment of the invention, there is yet further provided a method wherein the translating and the using is applied to a use case involving identifying patients to be added to a defined population of patients.

In accordance with an embodiment of the invention, there is yet further provided a method wherein the translating and the using are applied to a use case involving monitoring a population of patients including determining if they need to be evaluated, evaluating them thereby to generate at least one evaluation result, and responding to the evaluation result.

In accordance with an embodiment of the invention, there is yet further provided a method wherein the health information encoding procedure includes mapping health information expressed in at least one local terminology to a baseline terminology to enable terminology interoperability and storing ontological information interrelating health information items expressed in the baseline terminology.

In accordance with an embodiment of the invention, there is yet further provided a system wherein the ontological apparatus includes interrelationships between clinical-level information items.

In accordance with an embodiment of the invention, there is yet further provided a system wherein the clinical-level information item comprises at least one health care information item specifying at least one of a disease, rather than only a class thereof, and a medication, rather than only a class thereof, such as "Left Ventricular Heart Failure", rather than "Cardio-vascular disorder", and "Amoxicillin 250 MG Oral Capsule [Amoxymed]", rather than "Antibiotic", respectively.

In accordance with an embodiment of the invention, there is yet further provided a system wherein the ontological apparatus maps at least one legacy concept expressed in local terminology to at least one ontology concept expressed in a baseline terminology thereby allowing queries on the level of a single legacy concept to be responded to, for example, the following legacy concept: (System: ICD9, Code: 428.9, Designation: HEART FAILURE NOS) may be mapped to the following Ontology concept: (System: SNOMED-CT; Code: 84114007; Designation: Heart failure (disorder). Very generic examples of classifications are "Disorder", "Medicine", "Procedure"; more specific classification examples are "Cardio-vascular disorder", "Antibiotics" etc. Classifications do not identify a patient's clinical status; for example, it is not enough to say in a clinical record that the patient has "Cardio-vascular disorder" as there are many types of such disorders, and it is typically useful to know which disorder the patient suffers from, to decide how to treat it. Examples of clinical-level information items are "Left Ventricular Heart Failure", "Amoxicillin 250 MG Oral Capsule [Amoxymed]"; these information items are sufficiently detailed to describe aspects of an individual patient's clinical status and/or treatment rather than mere classifications thereof.

Also provided is a computer program product, comprising a typically non-transitory computer usable medium or computer readable storage medium, typically tangible, having a computer readable program code embodied therein, said computer readable program code adapted to be executed to implement any or all of the methods shown and described herein. It is appreciated that any or all of the computational steps shown and described herein may be computer-implemented. The operations in accordance with the teachings herein may be performed by a computer specially constructed for the desired purposes or by a general purpose computer specially configured for the desired purpose by a computer program stored in a typically non-transitory computer readable storage medium.

Any suitable processor, display and input means may be used to process, display e.g. on a computer screen or other computer output device, store, and accept information such as information used by or generated by any of the methods and apparatus shown and described herein; the above processor, display and input means including computer programs, in accordance with some or all of the embodiments of the present invention. Any or all functionalities of the invention shown and described herein may be performed by a conventional personal computer processor, workstation or other programmable device or computer or electronic computing device, either general-purpose or specifically constructed, used for processing; a computer display screen and/or printer and/or speaker for displaying; machine-readable memory such as optical disks, CDROMs, magnetic-optical discs or other discs; RAMs, ROMs, EPROMs, EEPROMs, magnetic or optical or other cards, for storing, and keyboard or mouse for accepting. The term "process" as used above is intended to include any type of computation or manipulation or transformation of data represented as physical, e.g. electronic, phenomena which may occur or reside e.g. within registers and /or memories of a computer. The term processor includes a single processing unit or a plurality of distributed or remote such units.

The above devices may communicate via any conventional wired or wireless digital communication means, e.g. via a wired or cellular telephone network or a computer network such as the Internet.

The apparatus of the present invention may include, according to certain embodiments of the invention, machine readable memory containing or otherwise storing a program of instructions which, when executed by the machine, implements some or all of the apparatus, methods, features and functionalities of the invention shown and described herein. Alternatively or in addition, the apparatus of the present invention may include, according to certain embodiments of the invention, a program as above which may be written in any conventional programming language, and optionally a machine for executing the program such as but not limited to a general purpose computer which may optionally be configured or activated in accordance with the teachings of the present invention. Any of the teachings incorporated herein may wherever suitable operate on signals representative of physical objects or substances.

The embodiments referred to above, and other embodiments, are described in detail in the next section.

Any trademark occurring in the text or drawings is the property of its owner and occurs herein merely to explain or illustrate one example of how an embodiment of the invention may be implemented.

Unless specifically stated otherwise, as apparent from the following discussions, it is appreciated that throughout the specification discussions, utilizing terms such as, "processing", "computing", "estimating", "selecting", "ranking", "grading ", "calculating", "determining", "generating", "reassessing", "classifying", "generating", "producing", "stereo-matching", "registering", "detecting", "associating", "superimposing", "obtaining" or the like, refer to the action and/or processes of a computer or computing system, or processor or similar electronic computing device, that manipulate and/or transform data represented as physical, such as electronic, quantities within the computing system's registers and/or memories, into other data similarly represented as physical quantities within the computing system's memories, registers or other such information storage, transmission or display devices. The term "computer" should be broadly construed to cover any kind of electronic device with data processing capabilities, including, by way of non-limiting example, personal computers, servers, computing system, communication devices, processors (e.g. digital signal processor (DSP), microcontrollers, field programmable gate array (FPGA), application specific integrated circuit (ASIC), etc.) and other electronic computing devices.

The present invention may be described, merely for clarity, in terms of terminology specific to particular programming languages, operating systems, browsers, system versions, individual products, and the like. It will be appreciated that this terminology is intended to convey general principles of operation clearly and briefly, by way of example, and is not intended to limit the scope of the invention to any particular programming language, operating system, browser, system version, or individual product.

Elements separately listed herein need not be distinct components and alternatively may be the same structure.

Any suitable input device, such as but not limited to a sensor, may be used to generate or otherwise provide information received by the apparatus and methods shown and described herein. Any suitable output device or display may be used to display or output information generated by the apparatus and methods shown and described herein. Any suitable processor may be employed to compute or generate information as described herein e.g. by providing one or more modules in the processor to perform functionalities described herein. Any suitable computerized data storage e.g. computer memory may be used to store information received by or generated by the systems shown and described herein. Functionalities shown and described herein may be divided between a server computer and a plurality of client computers. These or any other computerized components shown and described herein may communicate between themselves via a suitable computer network.

With regard to drawings and detailed descriptions of embodiments and examples of the present invention, certain embodiments of the present invention are illustrated and described in detail in the incorporated patent publication of the priority patent document, namely, U.S. Patent Application Publication No. 2012/0215560, to which reference is now made as if such disclosure were set forth next herein.

It is appreciated that software components of the present invention including programs and data may, if desired, be implemented in ROM (read only memory) form including CD-ROMs, EPROMs and EEPROMs, or may be stored in any other suitable typically non-transitory computer-readable medium such as but not limited to disks of various kinds, cards of various kinds and RAMs. Components described herein as software may, alternatively, be implemented wholly or partly in hardware, if desired, using conventional techniques. Conversely, components described herein as hardware may, alternatively, be implemented wholly or partly in software, if desired, using conventional techniques.

Included in the scope of the present invention, inter alia, are electromagnetic signals carrying computer-readable instructions for performing any or all of the steps of any of the methods shown and described herein, in any suitable order; machine-readable instructions for performing any or all of the steps of any of the methods shown and described herein, in any suitable order; program storage devices readable by machine, tangibly embodying a program of instructions executable by the machine to perform any or all of the steps of any of the methods shown and described herein, in any suitable order; a computer program product comprising a computer useable medium having computer readable program code, such as executable code, having embodied therein, and/or including computer readable program code for performing, any or all of the steps of any of the methods shown and described herein, in any suitable order; any technical effects brought about by any or all of the steps of any of the methods shown and described herein, when performed in any suitable order; any suitable apparatus or device or combination of such, programmed to perform, alone or in combination, any or all of the steps of any of the methods shown and described herein, in any suitable order; electronic devices each including a processor and a cooperating input device and/or output device and operative to perform in software any steps shown and described herein; information storage devices or physical records, such as disks or hard drives, causing a computer or other device to be configured so as to carry out any or all of the steps of any of the methods shown and described herein, in any suitable order; a program pre-stored e.g. in memory or on an information network such as the Internet, before or after being downloaded, which embodies any or all of the steps of any of the methods shown and described herein, in any suitable order, and the method of uploading or downloading such, and a system including server/s and/or client/s for using such; and hardware which performs any or all of the steps of any of the methods shown and described herein, in any suitable order, either alone or in conjunction with software. Any computer-readable or machine-readable media described herein is intended to include non-transitory computer- or machine-readable media.

Any computations or other forms of analysis described herein may be performed by a suitable computerized method. Any step described herein may be computer-implemented. The invention shown and described herein may include (a) using a computerized method to identify a solution to any of the problems or for any of the objectives described herein, the solution optionally include at least one of a decision, an action, a product, a service or any other information described herein that impacts, in a positive manner, a problem or objectives described herein; and (b) outputting the solution.

Features of the present invention which are described in the context of separate embodiments may also be provided in combination in a single embodiment. Conversely, features of the invention, including method steps, which are described for brevity in the context of a single embodiment or in a certain order may be provided separately or in any suitable subcombination or in a different order. "e.g." is used herein in the sense of a specific example which is not intended to be limiting. Devices, apparatus or systems shown coupled in any of the drawings may in fact be integrated into a single platform in certain embodiments or may be coupled via any appropriate wired or wireless coupling such as but not limited to optical fiber, Ethernet, Wireless LAN, HomePNA, power line communication, cell phone, PDA, Blackberry GPRS, Satellite including GPS, or other mobile delivery. It is appreciated that in the description and drawings shown and described herein, functionalities described or illustrated as systems and sub-units thereof can also be provided as methods and steps there within, and functionalities described or illustrated as methods and steps there within can also be provided as systems and sub-units thereof. The scale used to illustrate various elements in the drawings is merely exemplary and/or appropriate for clarity of presentation and is not intended to be limiting.

What is claimed is:

1. A method of providing health information of a patient from a health information exchange (HIE) system for view by a health provider with health information of the patient from an instance of an EMR application of an EMR system of the health provider, the method comprising:
   (a) running on a computerized device an instance of an agent application that is bound to the instance of the EMR application running on the computerized device;
   (b) determining context by screen scraping by the agent application instance information displayed by the EMR application instance, wherein the screen scraping by the agent application instance is a context interception process which determines a patient context within the EMR application instance in order to acquire and display the health information of the patient within the HIE system; and
   (c) responsive to the health provider using the EMR application instance running on the computerized device to acquire the health information of the patient from the EMR system of the EMR application instance and display it within a graphic user interface generated by the EMR application instance running on the computerized device, and further responsive to determining the context, acquiring by the agent application instance running on the computerized device the health information of the patient from the HIE system and displaying it within a graphic user interface generated by the agent application instance running on the computerized device.

2. The method of claim 1, wherein the graphic user interface generated by the agent application instance is transitionable between an expanded view for viewing of the health information of the patient from the HIE system with the health information of the patient from the EMR system, and a collapsed view for viewing of the health information of the patient from the EMR system without viewing the health information of the patient from the HIE system.

3. The method of claim 2, further comprising providing a flashing alert by the agent application instance when the graphic user instance is not in the expanded view prompting a health provider to transition the graphic user interface to the expanded view.

4. The method of claim 1, wherein the flashing alert is provided by the agent application instance when health information of the patient that is not from the EMR system has been acquired from the HIE system.

5. The method of claim 1, further comprising determining by the agent application instance a context of use within the EHR application instance.

6. The method of claim 1, further comprising determining by the agent application instance a patient context and current workflow within the EHR application instance.

7. The method of claim 1, further comprising providing by the agent application instance event notifications for view by a health provider.

8. The method of claim 1, further comprising acquiring and displaying by the agent application instance health information from the HIE system for a population of patients.

9. The method of claim 1, further comprising filtering from display by the agent application instance health information of the patient acquired from the HIE system that is duplicative of health information of the patient from the EMR system.

10. The method of claim 9, wherein health information of the patient acquired from the HIE system is determined to be duplicative of health information of the patient from the EMR system based on defined semantic relationships.

11. The method of claim 1, further comprising mimicking by the agent application instance a display operation of the display window containing the graphic user interface generated by the EMR application instance such that when the display window containing the graphic user interface generated by the EMR application instance is minimized, the graphic user interface generated by the agent application instance also is minimized concurrently therewith.

12. The method of claim 1, further comprising mimicking by the agent application instance a display operation of the display window containing the graphic user interface generated by the EMR application instance such that when the display window containing the graphic user interface generated by the EMR application instance is moved, the graphic user interface generated by the agent application instance also is moved concurrently therewith.

13. The method of claim 1, wherein the graphic user interface generated by the agent application instance is contained within a second display window that is displayed on top of the display window containing the graphic user interface generated by the EMR application instance.

14. The method of claim 1, further comprising mimicking the docking of the graphic user interface generated by the agent application instance within the display window containing the graphic user interface generated by the EMR application instance.

15. The method of claim 1, wherein the agent application instance selectively displays health information of the patient acquired from the HIE system.

16. The method of claim 15, wherein the agent application instance filters from display health information of the patient acquired from the HIE system that is from the EMR system.

17. The method of claim 16, further comprising selectively enabling and disabling through a user control the filtering of the health information of the patient by the agent application instance.

18. The method of claim 1, wherein the graphic user interface generated by the agent application instance floats on and is bound within a display window containing the graphic user interface generated by the EMR application instance such that the health information of the patient from the HIE system is displayed with the health information of the patient from the EMR system for concurrent viewing by the health provider.

19. A method of providing health information of a patient from a health information exchange (HIE) system for view by a health provider with health information of the patient from an instance of an EMR application of an EMR system of the health provider, the method comprising:
  (a) running on a computerized device an instance of an agent application that is bound to the instance of the EMR application running on the computerized device;
  (b) determining context by screen scraping by the agent application instance information displayed by the EMR application instance, wherein the screen scraping by the agent application instance is a context interception process to intercept context from the EMR application instance, the context comprising an indication of the patient, the context interception process using the indication of the patient in order to acquire and display the health information of the patient from the HIE system; and
  (c) responsive to the health provider using the EMR application instance running on the computerized device to acquire the health information of the patient from the EMR system of the EMR application instance and display it within a graphic user interface generated by the EMR application instance running on the computerized device, acquiring by the agent application instance running on the computerized device the health information of the patient from the HIE system and displaying it within a graphic user interface generated by the agent application instance running on the computerized device.

* * * * *